United States Patent [19]

Nair et al.

[11] 4,021,545

[45] May 3, 1977

[54] COMPLEMENT INHIBITORS

[75] Inventors: Vijay Gopalan Nair, Nanuet, N.Y.; Joseph Peter Joseph, Cliffside Park, N.J.; Seymour Bernstein, New City, N.Y.

[73] Assignee: American Cyanamid Company, Stamford, Conn.

[22] Filed: July 12, 1976

[21] Appl. No.: 704,586

[52] U.S. Cl. .................................. 424/180; 536/4; 536/118

[51] Int. Cl.² ........................................ A61K 31/70

[58] Field of Search ................ 424/180; 536/4, 118

[56] References Cited

UNITED STATES PATENTS 3,951,949  4/1976  Hamuro ............................ 424/180

Primary Examiner—Lewis Gotts
Assistant Examiner—Cary Owens
Attorney, Agent, or Firm—Jack W. Richards

[57] ABSTRACT

Inulin poly(H-sulfate) and salts thereof useful as complement inhibitors.

6 Claims, No Drawings

COMPLEMENT INHIBITORS

BACKGROUND OF THE INVENTION

The present invention resides in the concept of the use of inulin poly(H-sulfate) and salts thereof as inhibitors of the complement system of warm-blooded animals.

Inulin is a polysaccharide closely allied with starch and its structure may be found in the Merck Index, 8th Ed. pp. 568-569 (1968). Inulin itself has been used as a diagnostic agent to test renal function. Recently, inulin has been reported as an activator of the complement system, *Infection and Immunity*, 11: 273-279 (1975). Poly(H-sulfate)salts of inulin are known. U.S. Pat. Nos. 2,686,779 and 2,697,093 both disclose alkali metal sulfates of inulin and processes for their preparation. As noted in the aforementioned patents, alkali metal sulfates of inulin having varying degrees of sulfation have found application in the chemical industry as thickeners for pastes, as adhesives and as additives for muds used in the drilling of oil wells. Inulin sulphuric acid esters have been reported to be anticoagulants, *Arkiv for kemi, mineralogi o. geologi.*, Bd 24B. No. 5, pp. 1-4 (1946). Inulin sulfate has been reported to possess antilipemic activity, *Arch. int. pharmacodyn*, XCIX, 334 (1954).

It is known that certain polysaccharides and derivatives thereof process anti-complementary activity. For example, the sulphated polysaccharide heparin, and various salts thereof, have been reported to possess anticomplementary action, *J. Infect. Dis.*, 44: 250-253 (1929); *Acta. Med. Scand.*, 91: 550-554 (1937); Nature, 168: 563-564 (1951); *British J. Exp. Path.*, 33: 327-339 (1952); *Int. Congr. Chemother. Proc.* 5th (1967), 6, 191-196; and *Clin. Res.* 21: 877 (1973). Other sulphated polysaccharides, e.g., carrageenin and pentosan polysulphate have been reported as anti-complement agents. *Immunology*, 8:29 (1965) and *Pharmacology*, 9:74 (1973).

It has not heretofore been known, however, that the poly(H-sulfate)salts of inulin possess anticomplementary activity. Such is particularly surprising in view of the fact that the free polysaccharide inulin has been reported to acticate the complement system, *Infection and Immunity*, ibid.

The term complement refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r, and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. The standard reference for nomenclature of complement is *Bull. World Health Org.*, 39, 935-938, (1968). A more detailed discussion of the complement system and its role in body processes can be found in, for example, *Scientific American*, 229, (No. 5), 54-66 (1973); *Medical World News*, October 11, 1974, pp. 53-58; 64-66; *Harvey Lectures*, 66, 75-104 (1972); *The New England Journal of Medicine*, 287, 489-495; 545-549; 592-596; 642-646 (1972); *The John Hopkins Med. J.*, 128, 57-74 (1971); and *Federation Proceedings*, 32, 134-137 (1973).

The complement system can be considered to consist of three subsystems, (1) a recognition unit (C1q) which enables it to combine with antibody molecules that have detected a foreign invader; (2) an activation unit, (C1r, C1s, C2, C4, C3); which prepares a site on the neighboring membrane; and (3) an attack unit (C6, C7, C8, C9) which creates a hole in the membrane. The membrane attack unit is nonspecific; it destroys invaders only because it is generated in their neighborhood in order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex ciseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in Annual Review of Biochemistry, 38, 389 (1969).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), *The New England Journal of Medicine*, 286, 808–812, (1972); *Allergol, Et. Immunopath.*, II, 163–168 (1974); and *J. Allergy Clin. Immunol.*, 53, No. 5, 298–302 (1974).

SUMMARY OF THE INVENTION

It has now been discovered that poly(H-sulfate)salts of inulin interact with the complement reaction sequence, thereby inhibiting complement activity in body fluids.

This invention is particularly concerned with all pharmaceutically acceptable inulin poly(H-sulfate)-polysalts having complement inhibiting activity. Representative of such inulin poly(H-sulfate)polysalts are the following: Inulin, poly(H-sulfate)sodium salt; Inulin, poly(H-sulfate)polysalt with trimethylamine; Inulin, poly(H-sulfate)polysalt with triethylamine; Inulin, poly(H-sulfate)potassium salt.

The poly(H-sulfate)salts of inulin may be represented by the following formula:

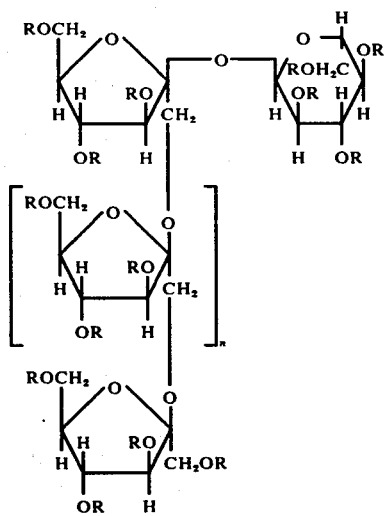

wherein R is selected from the group comprising —$SO_3A$ and —$SO_3^-$ $HR'^+$, wherein A is hydrogen, alkaline earth or alkali metal; R' is triloweralkyl ($C_1$–$C_8$) amine and n is 20 through 35. The poly(H-sulfate)salts of inulin contemplated by the present invention are the completely sulphated salts.

The poly(H-sulfate) salts of inulin of this invention may be prepared by the application or adaptation of known methods described in U.S. Pat. Nos. 3,271,388; 2,923,704 2,686,779; and 2,697,093, or *Chemical Reviews*, 62:549 (1962) As illustrative, an appropriate triloweralkylamine-sulfur trioxide complex is dissolved in dimethylformamide with heat (65°–70° C) until a clear solution is obtained. Inulin is added and the mixture is stirred with heat. The product forms as a gum and is allowed to stand several hours. The gum is recovered and triturated with dimethylformamide and then absolute ethanol which produces a granular solid product. The alkali metal or alkaline earth salts may be prepared from the above product using the appropriate salt.

This invention is also concerned with a method of inhibiting the complement system in a body fluid, such as blood serum, which comprises subjecting body fluid complement to the action of an effective complement inhibiting amount of a poly(H-sulfate)polysalt of inulin. The method of use aspect of this invention is also concerned with a method of inhibiting the complement system in a warm-blooded animal which comprises internally administering to said animal an effective complement inhibiting amount of a poly(H-sulfate)salt of inulin. Body fluid can include blood, plasma, serum, synovial fluid, cerebrospinal fluid, or pathological accumulations of fluid such as pleural effusion, etc.

The poly(H-sulfate)salts of inulin of the present invention find utility as complement inhibitors in body fluids and as such may be used to ameliorate or prevent those pathological reactions requiring the function of complement and in the therapeutic treatment of warm-blooded animals having immunological diseases such as rheumatoid arthritis, systemic lupus erythematosus, certain kinds of glomerulonephritis, certain kinds of auto-allergic hemolytic anemia, certain kinds of platelet disorders and certain kinds of vasculitis. Poly(H-sulfate)salts of inulin may also be used in the therapeutic treatment of warm-blooded animals having non-immunologic diseases such as paroxysmal nocturnal hemoglobinuria, hereditary angioneurotic edema (treated by Suramin Sodium, etc.) and inflammatory states induced by the action of bacterial or lysosomal enzymes on the appropriate complement components as for example, inflammation following coronary occlusion. They may also be useful in the treatment of transplant rejection and as blood culture and transport mediums.

DETAILED DESCRIPTION OF THE INVENTION

The following examples describe in detail the preparation and formulation of representative compounds of the present invention.

EXAMPLE 1

Inulin, poly(H-sulfate)salt with trimethylamine

A 11.5 g portion of trimethylamine-sulfur trioxide complex is dissolved in 75 ml of dimethylformamide with stirring at 65°–70° C until a clear solution is obtained. A 4.0 g portion of inulin is added and the mixture is stirred at 65° C. The solution gradually turns cloudy and a thick gum separates. The reaction mixture is allowed to stand 20 hours. The supernatant is discarded. The gum is triturated with dimethylformamide and then with absolute ethanol resulting in a colorless granular solid. This solid is filtered and washed repeatedly with absolute ethanol and anhydrous ether and then dried. The product is a colorless granular solid.

EXAMPLE 2

Inulin, poly(H-sulfate)sodium salt

A 19.0 g portion of the trimethylammonium salt of inulin poly(H-sulfate) is dissolved in 50 ml of water and 75 ml of 30% aqueous sodium acetate solution is added. The solution is filterd to clarify and allowed to stand for about 10 minutes. A 250 ml portion of absolute ethanol is added to the clear filtrate. A thick gum separates. After standing a few minutes, more absolute ethanol is added to ensure complete precipitation. The supernatant is removed and the gum on trituration with absolute ethanol becomes a colorless granular solid which is filtered and washed four times with absolute ethanol and twice with anhydrous ether. The resulting solid is redissolved in 50 ml of water and the entire procedure described above is repeated. The product is a colorless granular solid.

EXAMPLE 3

Inulin, poly(H-sulfate)salt with triethylamine

A 2.0 g portion of triethylamine-sulfur trioxide complex is dissolved in 15 ml of dimethylformamide with stirring at 60° C. A 500 mg portion of inulin is added and the mixture is stirred at 60° C for 24 hours. The solution is cooled to room temperature and 150 ml of dry acetone is added, resulting in the precipitation of a finely divided colorless solid. The product is recovered by filtration and dried. On storage it turns into transparent prisms.

EXAMPLE 4

Preparation of Compressed Tablet

| INGREDIENT | MG/TABLET |
|---|---|
| Inulin, poly(H-sulfate)sodium salt | 0.5–500 |
| Dibasic Calcium Phosphate N.F. | qs. |
| Starch USP | 40 |
| Modified Starch | 10 |
| Magnesium Stearate USP | 1–5 |

EXAMPLE 5

Preparation of Compressed Tablet
Sustained Action

| INGREDIENT | MG/TABLET |
|---|---|
| Inulin, poly(H-sulfate)sodium salt | 0.5–500 |
| Dibasic Calcium Phosphate N.F. | qs. |
| Alginic Acid | 20 |
| Starch USP | 35 |
| Magnesium Stearate USP | 1–10 |

EXAMPLE 6

Preparatin of Hard Shell Capsule

| INGREDIENT | MG/CAPSULE |
|---|---|
| Inulin, poly(H-sulfate)salt with triethylamine | 0.5–500 |
| Lactose, Spray Dried | qs. |
| Magnesium Stearate | 1–10 |

EXAMPLE 7

Preparation of Oral Liquid (Syrup)

| INGREDIENT | % W/V |
|---|---|
| Inulin, poly(H-sulfate)salt with triethylamine | 0.0–5 |
| Liquid Sucrose (70%) | 75.0 |
| Methyl Paraben USP | 0.18 |
| Propyl Paraben USP | 0.02 |
| Flavoring Agent | qs. |
| Purified Water qs ad | 100.0 |

EXAMPLE 8

Preparation of Oral Liquid (Elixir)

| INGREDIENT | % W/V |
|---|---|
| Inulin, poly(H-sulfate)salt with triethylamine | 0.05–5 |
| Alcohol USP | 12.5 |
| Glycerin USP | 45.0 |
| Flavoring Agent | qs. |
| Purified Water qs ad | 100.0 |

EXAMPLE 9

Preparation of Oral Suspension (Syrup)

| INGREDIENT | % W/V |
|---|---|
| Active Component* | 0.05–5 |
| Polysorbate 80 USP | 0.1 |
| Magnesium Aluminum Silicate, Colloidal | 0.3 |
| Flavoring Agent | qs. |
| Methyl Paraben USP | 0.18 |
| Propyl Paraben USP | 0.02 |
| Liquid Sucrose (70%) | 75.0 |
| Purified Water qs ad | 100.0 |

*Inulin, poly(H-sulfate) salt with trimethylamine as Aluminum Lake, Micronized

EXAMPLE 10

Preparation of Injectable Solution

| INGREDIENT | % W/V |
|---|---|
| Inulin, poly(H-sulfate)sodium salt | 0.05–5 |
| Benzyl Alcohol N.F. | 0.9 |
| Water for Injection qs ad | 100.0 |

EXAMPLE 11

Preparation of Injectable Oil

| INGREDIENT | % W/V |
|---|---|
| Inulin, poly(H-sulfate)sodium salt | 0.05–5 |
| Benzyl Alcohol N.F. | 1.5 |
| Sesame Oil qs ad | 100.0 |

EXAMPLE 12

Preparation of Injectable Depo Suspension

| INGREDIENT | % W/V |
|---|---|
| Inulin, poly(H-sulfate)sodium salt as Aluminum Lake Micronized | 0.05–5 |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs. |
| Water for Injection qs ad | 100.0 |

EXAMPLE 13

| Intra-articular Preparation | |
|---|---|
| INGREDIENT | |
| Inulin, poly(H-sulfate)sodium salt (micronized) | 2–20 mg |
| NaCl (physiological saline) | 0.9% |
| Benzyl alcohol | 0.9% |
| *Sodium carboxymethylcellulose pH adjused to 5.0–7.5 | 1–5% |
| Water for injection qs to | 100% |

*Increasing the NaCMe forms a syrupy solution of water-soluble compounds.

The inulin poly(H-sulfate)salts which are the essence of this invention may be administered internally, e.g., orally or parenterally, e.g., intra-articularly to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for the intravenous or subcutaneous use from about 5 to about 50 mg/kg/day, or every six hours for more rapidly excreted salts, may be used. For intra-articular use for large joints, such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the salt can contain from about 0.5 mg to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e. oral or parenteral. The compounds can be used in compositions such as tablets. Here, the principal active ingredient is mixed with conventional tableting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The pills may be colored (e.g. pink) through use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor). This test measures the ability of activated human C1 to destroy fluid phase human C2 in the presence of C4 and appropriate dilutions of the test compound. An active inhibitor protects C2 from C1 and C4; (ii) Test, Code 035 (C3-C9 inhibitor) — This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C - Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported unless otherwise stated; (v) Forssman Shock — Lethal shock is produced in guinea pigs by an I.V. injection of anti-Forssman antiserum. The harmonic mean death time of treated guinea pigs is compared with that of simultaneous controls; (vi) Complement Level Reduction Test — In this test, the above dosed guinea pigs, or others are bled for serum. The complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run.

With reference to Table I, guinea pigs weighing about 300 g were dosed intravenously (IV) or intraperitoneally (IP) with 200 mg/kg of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of in vitro tests, code 026, 035 and 036 and the Cap 50 test. Table I shows that the compounds of the invention possess complement inhibiting activity.

TABLE I

| | Biological Activity | | | | In Vivo Activity Guinea Pig (IV) | | |
|---|---|---|---|---|---|---|---|
| Compound | Cl 026* | C-Late 035 | Shunt Inhibit. 036 | Cap 50 | 2 Hr. | 30 Hr. | 120 Hr. |
| INULIN, POLY-(H-SULFATE) SODIUM SALT | 7** | 5 | 5 | 100 | — | — | — |
| | — | — | — | 94 | — | — | — |
| | 10 | 7 | 5 | 92 | — | — | — |
| INULIN, POLY-(H-SULFATE)-SALT WITH TRI-METHYLAMINE | 8 | 6 | 5 | 131 | — | — | — |
| INULIN, POLY-(H-SULFATE)-SALT WITH TRI-ETHYLAMINE | 8 | 5 | 5 | 160 | −97 | −95 | −91 |

*Tests identifed by codes herein.
**Numbers represent activity in wells, a serial dilution assay, higher well number indicates higher activity. The serial dilutions are two-fold.

We claim:

1. A method of inhibiting the complement system in a body fluid which comprises subjecting said body fluid to the action of an effective complement inhibiting amount of a compound selected from those of the formula:

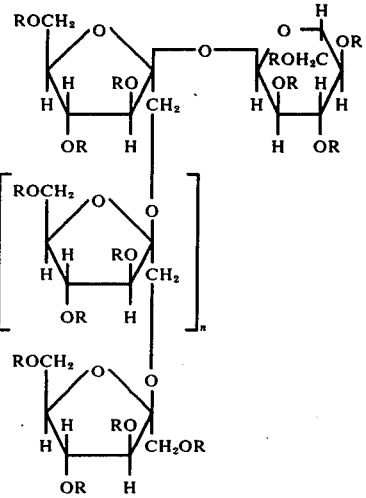

wherein R is selected from the group comprising —$SO_3A$ and —$SO_3^-$ $HR'^+$, wherein A is hydrogen, alkaline earth or alkali metal; R' is triloweralkyl ($C_1$–$C_6$) amine; and n is 20 through 35.

2. A method according to claim 1 wherein the compound is inulin, poly(H-sulfate)sodium salt.

3. A method of claim 1 wherein the compound is inulin, poly(H-sulfate)sodium salt with triloweralkyl ($C_1$–$C_6$) amine.

4. A method of inhibiting the complement system in a warm-blooded animal which comprises administering to said animal an effective complement inhibiting amount of a compound selected from those of the formula:

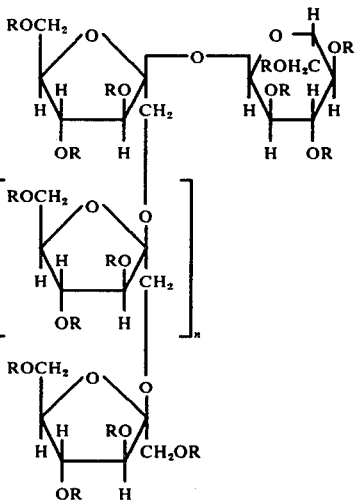

wherein R is selected from the group comprising —$SO_3A$ and —$SO_3^-$ $HR'^+$, wherein A is hydrogen, alkaline earth or alkali metal; R' is triloweralkyl ($C_1$–$C_6$) amine; and n is 20 through 35.

5. A method according to claim 4 wherein the compound is inulin, poly(H-sulfate)sodium salt.

6. A method according to claim 4 wherein the compound is inulin, poly(H-sulfate)salt with triloweralkyl ($C_1$–$C_6$) amine.

* * * * *